United States Patent [19]

Sipos

[11] 4,035,567
[45] July 12, 1977

[54] PROCESS FOR PRODUCING THE METHYL ESTER OF AMPHOTERICIN B

[75] Inventor: Frank Sipos, Princeton, N.J.

[73] Assignee: E. R. Squibb & Sons, Inc., Princeton, N.J.

[21] Appl. No.: 624,508

[22] Filed: Oct. 21, 1975

[51] Int. Cl.² ........................................ C07H 17/08
[52] U.S. Cl. ..................................... 536/4; 536/17; 536/115
[58] Field of Search ........ 260/234, 210 AB, 210 R; 536/115, 4, 17

[56] References Cited

U.S. PATENT DOCUMENTS 2,908,612  10/1959  Dutcher et al. ............. 260/210 AB
3,945,993  3/1976  Schaffner et al. .................... 536/17

OTHER PUBLICATIONS

Noller "Chemistry of Organic Compounds" 3rd Ed. W. B. Saunders Co., Phila, Pa., 1965, p. 184.

Primary Examiner—Johnnie R. Brown
Attorney, Agent, or Firm—Lawrence S. Levinson; Merle J. Smith; Burton Rodney

[57] ABSTRACT

A process is provided for producing amphotericin B methyl ester wherein amphotericin B is initially mixed and suspended in dimethylformamide or hexamethylphosphoric triamide for a predetermined period, and thereafter aqueous ammonia is slowly added to the mixture until a clear solution is obtained. The dissolved amphotericin B is then esterified with diazomethane in accordance with conventional procedures.

4 Claims, No Drawings

PROCESS FOR PRODUCING THE METHYL ESTER OF AMPHOTERICIN B

The present invention relates to a process for producing the methyl ester of amphotericin B wherein dimethylformamide or hexamethylphosphoric triamide is employed in initially dissolving the amphotericin B starting material.

The methyl ester of amphotericin B which has the formula

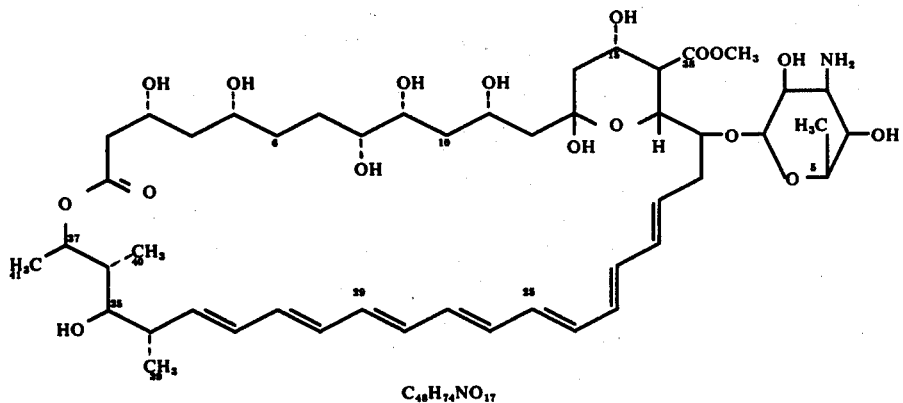

$C_{48}H_{74}NO_{17}$ has been prepared by mixing amphotericin B starting material with dimethylsulfoxide and methanol to form a solution of the amphotericin B. The dissolved amphotericin B is then esterified by reaction with diazomethane and the resulting reaction mixture treated with ethyl ether to precipitate the methyl ester.

Belgian Pat. No. 802,512 discloses another procedure for preparing the methyl ester of amphotericin B wherein amphotericin B starting material is mixed with dimethylsulfoxide to form a solution and aqueous ammonia is added to adjust the pH to about 10 (measured on wet indicator paper or after dilution of a sample with water). The solution of amphotericin B is then treated with diazomethane as described above to form the methyl ester.

In view of the objections raised against use of dimethylsulfoxide in connection with the manufacture of medicaments, it has been suggested to replace dimethylsulfoxide with other solvent systems for amphotericin B. However, where it has been attempted to substitute dimethylformamide for the dimethylsulfoxide in the procedures outlined above, it has been found that the amphotericin B will not dissolve.

In accordance with the present invention, a process is provided for producing the methyl ester of amphotericin B in a homogeneous medium which is free of dimethylsulfoxide and the product is substantially more stable than the methyl ester prepared by the aforementioned processes which utilize dimethylsulfoxide.

The process of the present invention comprises mixing amphotericin B starting material with dimethylformamide or hexamethylphosphoric triamide, for a predetermined period, and thereafter mixing the above with sufficient aqueous ammonia to obtain a solution of the amphotericin B, such solution having a pH above 9 in the case where dimethylformamide is used and a pH above 10 in the case where hexamethylphosphoric triamide is used, the pH being measured after dilution of a sample wih water or dropping on wet indicator paper.

Where dimethylformamide is employed in the process of the invention, the dimethylformamide will be employed in a weight ratio to the amphotericin B of within the range of from about 10:1 to about 15:1, and preferably from about 12:1 to about 14:1. The mixture of amphotericin B and dimethylformamide will preferably be stirred for a period ranging from about 5 minutes to about 2 hours, and most preferably for from about 10 minutes to about 1 hour prior to adding aqueous ammonia to the mixture. It has been found that if the aqueous ammonia is added immediately after suspending the amphotericin B in the dimethylformamide, a solution is not obtained.

Where hexamethylphosphoric triamide is employed, the aqueous ammonia may be added immediately after suspending the amphotericin B in the hexamethylphosphoric triamide to achieve complete dissolution. The hexamethylphosphoric triamide will be employed in a weight ratio to the amphotericin B of within the range of from about 7:1 to about 12:1, and preferably from about 8:1 to about 10:1.

After the dissolution of the amphotericin B is effected, esterification is carried out employing diazomethane in acordance with conventional techniques. The solution of amphotericin B is preferably cooled below room temperature, for example, within the range of from about 0° to about 15° C, and an excess of diazomethane (the excess ranging from about 100 to about 150 % over stoichiometric requirements) in a solvent such as tetrahydrofuran or ethyl ether, is added. After removal of solvents, for example, by evaporation, the residue is treated with a solvent, such as ethyl ether, to precipitate out the methyl ester of amphotericin B. The methyl ester so-obtained is thereafter purified by washing in solvents such as ethyl ether, acetone-ethyl ether mixtures and the like.

The following Examples represent preferred embodiments of the present invention. All temperatures are expressed in °C.

EXAMPLE 1

Preparation of Amphotericin B, Methyl Ester Employing Dimethylforamamide

In a 4 liter Erlenmeyer flask, 75 g (81 mMol) of amphotericin B is suspended in 1.1 liters of dimethylformamide (analytical grade) and stirred for 1 hour. The light yellow color of the suspension changes to ochre. Concentrated ammonium hydroxide (5 ml) is then added in portions to achieve complete dissolution. The solution is cooled to 5° C and a total of 7.85 g (187 mMol or 2.3 equivalents or 130% excess) of diazomethane in about 600 ml of tetrahydrofuran is added in 50 ml portions during a 30 minute period of time. Then the cooling bath is removed and the mixture stirred at room temperature for 2 hours. The bulk of the solvents are removed by evaporation in vacuo on a rotary evaporator at maximun bath temperature of 35°. The dark oily residue is then poured into 10 liters of absolute ether with intensive stirring. The resulting precipitate is filtered off on a 16 cm Buchner funnel fitted with Whatman SFC42 paper. The cake is washed with 2 liters of ethyl ether, 1 liter of acetone-ethyl ether (1:2) and again with 1 liter of absolute ethyl ether. The amphotericin B, methyl ester is dried in vacuo over $P_2O_5$ for 48 hours. The yield is 71.5 g (94%).

The methyl ester product has the following properties:

| | |
|---|---|
| Appearance | Amorphous powder |
| Color | Light yellow |
| Odor | Slight (unspecified) |
| Residual Solvents (VPC) | Dimethylformamide 0.17% |
| | Ethyl Ether ⎫ |
| | Acetone ⎬ <<0.1% |
| | Tetrahydrofuran ⎭ |
| | Water 5.3 |
| Elemental Analysis: | For $C_{46}H_{74}NO_{17} \cdot 3H_2O$ |
| | (m.w. 991.2) |
| | Calcd: |
| | 58.17%C 8.13%H 1.41%N |
| | 58.39%C 7.93%H |
| | 1.49%N |
| Ultraviolet Spectrum | max. at 343, 362, |
| | 380 and 403 mm |
| (0.25% DMSO in Methanol) | $E_{1cm}^{1\%}$ 1550 at 403 nm |
| X-ray pattern | |
| | Amorphous |
| Bioassay | 1200 γ/mg (as is basis) |
| Thin Layer Chromatography | |
| A) n-PrOH-conc. $NH_4OH$ (7.3 v/v) | Main component at |
| | $R_f$ 0.45 |
| | Five minor or trace |
| | impurities |
| B) n-BuOH-EtOH-$(CH_3)_2$CO- | Main component at |
| conc. $NH_4OH$ (2:5:1:3 v/v) | $R_f$ 0.60 |
| | Five to six minor or |
| | trace impurities |

The above esterification procedure is repeated five times. The bioassay data shows constant range of activity in all five batches (1171–1209 γ/mg).

EXAMPLE 2

Preparation of Amphotericin B, Methyl Ester Employing Hexamethylphosphoric Triamide Ten g of amphotericin B is suspended in 100 ml of hexamethylphosphoric triamide and with stirring concentrated ammonimum hydroxide is added dropwise until complete dissolution is achieved. The solution is cooled to 5° and an excess (~ 125%) of a titrated solution of diazomethane in tetrahydrofuran is added in 3–5 portions during 10–15 minutes. The mixture is stirred for 20 minutes and thereafter poured into 2 liters of ethyl ether. The resulting precipitate is stirred for 10 minutes, then filtered off, washed with ethyl ether (300 ml) and dried in vacuo at room temperature. The yield is about 70%.

The methyl ester product has properties similar to that described in Example 1.

What is claimed is:

1. A process for preparing the methyl ester of amphotericin B, which comprises mixing amphotericin B with hexamehylphosphoric triamide, wherein the hexamethylphosphoric triamide is employed in a weight ratio to the amphotericin B of within the range of from about 7:1 to about 12:1 and thereafter adding aqueous ammonia to the above mixture until dissolution of the amphotericin B occurs and the mixture has a pH of above 10, and esterifying the amphotericin B in solution with diazomethane to form the methyl ester of amphotericin B.

2. The process as defined in claim 1 wherein the aqueous ammonia is added immediately after the hexamethylphosphoric triamide is added to the amphotericin B.

3. The process as defined in claim 1 wherein the aqueous ammonia is slowly added to the mixture of hexamethylphosphoric triamide to form a clear solution of pH above 10.

4. A process for dissolving amphotericin B, which comprises mixing amphotericin B with hexamethylphosphoric triamide, wherein the hexamethylphosphoric triamide is employed in a weight ratio to the amphotericin B of within the range of from about 7:1 to about 12:1, and thereafter adding aqueous ammonia to the above mixture to form a clear solution of amphotericin B having a pH of above 10.

* * * * *

UNITED STATES PATENT OFFICE
CERTIFICATE OF CORRECTION

Patent No. 4,035,567      Dated July 12, 1977

Inventor(s) Frank Sipos

It is certified that error appears in the above-identified patent and that said Letters Patent are hereby corrected as shown below:

Column 1, line 59, after "above" insert --mixture--.
Column 2, line 60, "Dimethylforamamide" should read
  --Dimethylformamide--.
Column 3, line 37, "7.3" should read --7:3--.
Column 4, line 22, "hexamehylphosphoric" should read
  --hexamethylphosphoric--.

Signed and Sealed this

Eighth Day of November 1977

[SEAL]

Attest:

RUTH C. MASON
Attesting Officer

LUTRELLE F. PARKER
Acting Commissioner of Patents and Trademarks